(12) United States Patent
Von Oepen (10) Patent No.: US 8,808,235 B2
(45) Date of Patent: Aug. 19, 2014

(54) MEDICAL DEVICE SYSTEM AND METHOD FOR PUSHABILITY

(75) Inventor: Randolf Von Oepen, Aptos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 63 days.

(21) Appl. No.: 13/359,707

(22) Filed: Jan. 27, 2012

(65) Prior Publication Data

US 2013/0197432 A1     Aug. 1, 2013

(51) Int. Cl.
*A61M 25/14*     (2006.01)

(52) U.S. Cl.
USPC .............. 604/96.01; 604/164.12; 604/164.13; 604/165.01

(58) Field of Classification Search
CPC .......... A61M 25/0102; A61M 25/104; A61M 2025/0004; A61M 2025/0006; A61M 2025/0063
USPC ................. 604/96.01, 164.12, 164.13, 165.01
See application file for complete search history.

(56) References Cited

U.S. PATENT DOCUMENTS

| | | | |
|---|---|---|---|
| 4,748,982 A | 6/1988 | Horzewski et al. | |
| 4,877,031 A * | 10/1989 | Conway et al. | 606/194 |
| 5,300,085 A | 4/1994 | Yock | |
| 5,441,484 A * | 8/1995 | Atkinson et al. | 604/99.04 |
| 5,458,615 A | 10/1995 | Klemm et al. | |
| 5,464,650 A | 11/1995 | Berg et al. | |
| 5,496,346 A | 3/1996 | Horzewski et al. | |
| 5,507,768 A | 4/1996 | Lau et al. | |
| 5,591,227 A | 1/1997 | Dinh et al. | |
| 5,626,600 A | 5/1997 | Horzewski et al. | |
| 5,649,977 A | 7/1997 | Campbell | |
| 6,017,323 A * | 1/2000 | Chee | 604/96.01 |
| 6,406,457 B1 | 6/2002 | Wang et al. | |
| 7,303,798 B2 | 12/2007 | Bavaro et al. | |
| 7,322,959 B2 | 1/2008 | Warnack et al. | |
| 7,335,227 B2 | 2/2008 | Jalisi | |
| 7,378,105 B2 | 5/2008 | Burke et al. | |
| 7,445,792 B2 | 11/2008 | Toner et al. | |
| 7,833,597 B2 | 11/2010 | Bavaro et al. | |
| 7,967,836 B2 | 6/2011 | Warnack et al. | |
| 2005/0182475 A1 | 8/2005 | Jen et al. | |
| 2007/0088255 A1 | 4/2007 | Toner et al. | |
| 2008/0015499 A1 | 1/2008 | Warnack et al. | |
| 2010/0023108 A1 | 1/2010 | Toner et al. | |
| 2010/0030183 A1 | 2/2010 | Toner et al. | |
| 2011/0070355 A1 | 3/2011 | Bavaro et al. | |

* cited by examiner

*Primary Examiner* — Laura Bouchelle
(74) *Attorney, Agent, or Firm* — Baker Botts L.L.P.

(57) ABSTRACT

Medical device system comprising a catheter including an elongate tubular member having an inner wall surface defining a lumen extending longitudinally through at least a portion of the tubular member. The medical device also includes an inner stop extending inwardly from the inner wall surface of the tubular member at a distal end section of the catheter and a pusher device insertable into the lumen. The pusher device has a contact surface to abut the inner stop of the tubular member.

32 Claims, 6 Drawing Sheets

MEDICAL DEVICE SYSTEM AND METHOD FOR PUSHABILITY

BACKGROUND OF THE DISCLOSED SUBJECT MATTER

1. Field of the Disclosed Subject Matter

The disclosed subject matter relates to the intraluminal delivery of a medical device and a medical device system regarding the same. More particularly, the presently disclosed subject matter relates to a medical device system including a catheter and a pusher device insertable into a lumen of the catheter.

2. Description of Related Subject Matter

Intraluminal treatment thus often involves delivery of a catheter or delivery device through various body lumens. For example, but not limitation, various diseases and conditions of the vasculature can be treated using interventional devices such as catheters. Cardiovascular disease is prevalent in the United States and in other parts of the world. One manifestation of cardiovascular disease is atherosclerosis, which is the buildup of plaque (or fatty deposits) on the walls of blood vessels, such as coronary and peripheral arteries. This buildup of plaque can grow large enough to reduce or occlude blood flow through the blood vessel. Furthermore, serious damage can result if an area of plaque ruptures from the vessel wall and forms a clot, which can travel to another part of the body. If the blood vessels that feed the heart are blocked, a heart attack can result. If the blood vessels to the brain are blocked, a stroke can result.

Athersclerosis can be treated through the use of a balloon catheter to open the occlusion, using a technique generally known as angioplasty. Furthermore, physicians can treat atherosclerosis by implanting a tubular endoprosthesis such as a stent at the narrowed or blocked segment of the blood vessel. The endoprosthesis when expanded widens and holds open the blood vessel. To perform this procedure, the stent is delivered to the site of the lesion in the blood vessel by a catheter assembly, otherwise known as a stent delivery device. The stent delivery device enters the vasculature of the patient through the femoral artery and travels through a tortuous path to the site of the lesion. The physician positions the stent across the lesion and deploys the stent. In its expanded configuration, the stent can maintain the patency of the blood vessel. For details of example stents, see for example, U.S. Pat. No. 5,507,768 (Lau, et al.) and U.S. Pat. No. 5,458,615 (Klemm, et al.), which are incorporated herein by reference. A balloon catheter likewise can be used for subsequent stent placement in the vessel wall.

To position the balloon and/or stent at the lesion site, the catheter is designed to have suitable pushability (i.e., ability to transmit force along the length of the catheter), trackability, and flexibility, to be readily advanceable within the tortuous anatomy of the vasculature. However, given the tortuous path of the vascular system to the lesion site and the possibility of obstructions, for example, movement of the catheter or delivery device can be inhibited or precluded within the blood vessel. For example, plaque or the like can create a chronic total occlusion within the vessel, and thus prevent passage of the catheter or delivery device thereacross. Similar issues likewise arise in other body lumens.

Hence, there remains a need to develop a medical device system and method to assist in distal movement of a catheter within the vasculature or other body lumens of a patient.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve the above and other advantages and in accordance with the purpose of the disclosed subject matter, as embodied and broadly described, the disclosed subject matter provides according to one embodiment, a medical device system that includes a catheter including an elongate tubular member having an inner wall surface defining a lumen extending longitudinally through at least a portion of the tubular member. The medical device also includes an inner stop extending inwardly from the inner wall surface of the tubular member at a distal end section of the catheter and a pusher device insertable into the lumen. The pusher device has a contact surface to abut the inner stop of the tubular member.

According to a further aspect of the disclosed subject matter, there is provided a method of delivering a medical device, comprising providing a catheter including an elongate tubular member having an inner wall surface defining a lumen extending longitudinally through at least a portion of the tubular member and an inner stop extending inwardly from the inner wall surface of the tubular member at a distal end section of the catheter. The method further including positioning the catheter in a body lumen and inserting a pusher device into the lumen of the elongate tubular member, wherein the pusher device comprises a contact surface to abut against the inner stop of the tubular member.

It is to be understood that both the foregoing general description and the following detailed description are embodiments and are intended to provide further explanation of the disclosed subject matter claimed. The accompanying drawings, which are incorporated in and constitute part of this specification, are included to illustrate and provide a further understanding of the system and method of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which.

DETAILED DESCRIPTION

While the subject matter is capable of various modifications and alternative forms, specific embodiments thereof are depicted in the drawings, and will herein be described in detail for the purpose of illustration and not limitation. It should be understood, however, that it is not intended to limit the subject matter to the particular forms disclosed but, to the contrary, the intention is to cover all modifications, equivalents, and alternatives falling within the spirit and scope of the subject matter as defined by the appended claims. It will be apparent to those skilled in the art that various modifications and variations can be made to the catheter without departing from the spirit or scope of the subject matter. Thus, it is intended that the disclosed subject matter include modifications and variations that are within the scope of the appended claims and their equivalents.

In accordance with an aspect of the disclosed subject matter, a medical device system and a method of delivering the same is provided. The medical device system comprises a catheter including an elongate tubular member having an inner wall surface defining a lumen extending longitudinally through at least a portion of the tubular member. The medical device also includes an inner stop extending inwardly from the inner wall surface of the tubular member at a distal end section of the catheter and a pusher device insertable into the lumen. The pusher device has a contact surface to abut the inner stop of the tubular member.

In accordance with another aspect, a method of delivering a medical device is provided comprising providing a catheter including an elongate tubular member having an inner wall surface defining a lumen extending longitudinally through at least a portion of the tubular member and an inner stop extending inwardly from the inner wall surface of the tubular member at a distal end section of the catheter. The method further including positioning the catheter in a body lumen and inserting a pusher device into the lumen of the elongate tubular member, wherein the pusher device comprises a contact surface to abut against the inner stop of the tubular member.

For purpose of illustration and not limitation; reference will now be made in detail to specific embodiments, examples of which are illustrated in the accompanying drawings. For the purposes of this disclosure, like reference numbers in the figures shall refer to like features unless otherwise indicated and the device and method will be described in conjunction with each other.

Figure 1:
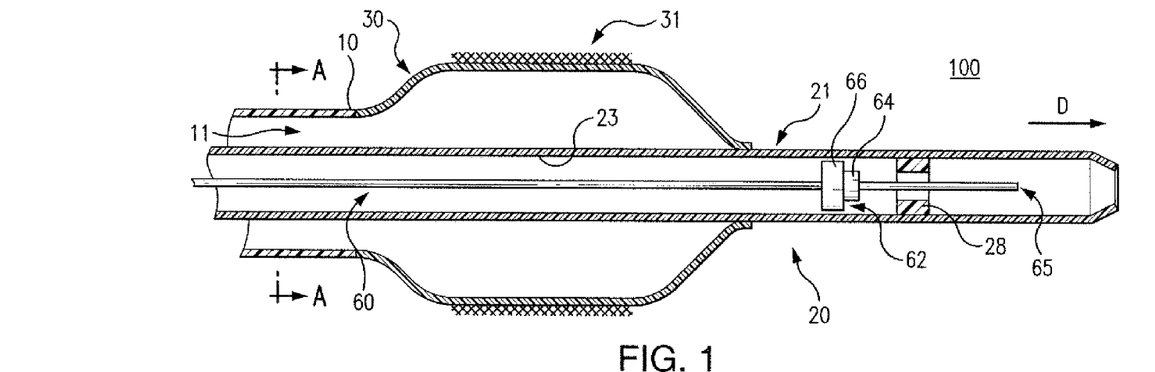
FIG. 1 is a schematic side view of a representative embodiment of a medical device system, according to an embodiment of the disclosed subject matter.

Referring to FIG. 1, there is shown a representative embodiment of a medical device system 100 including a catheter 20 which at least comprises an elongated tubular shaft having a proximal section and a distal section. Particularly, FIG. 1 depicts a distal section of a balloon catheter 20, although any of a variety of other types of catheters, including delivery systems, can be used in accordance with the disclosed subject matter.

The shaft of the catheter can be made of a variety of suitable configurations. For example, the shaft can provide an over the wire (OTW) configuration with the guidewire lumen extending generally across the entire length of the shaft. As an alternative embodiment, the shaft of the catheter can be a rapid exchange (RX) configuration with the guidewire lumen extending distally from a proximal guidewire port to or near the distal end of the shaft, as known in the art.

In either the OTW or RX configurations, the shaft can be a single piece multi-lumen member, or can include a co-axial arrangement. Similarly, the catheter can be a single lumen shaft configuration, such as for a self-expanding stent delivery system, or a multi-lumen configuration, such as for a balloon catheter or the like.

Figure 1A:
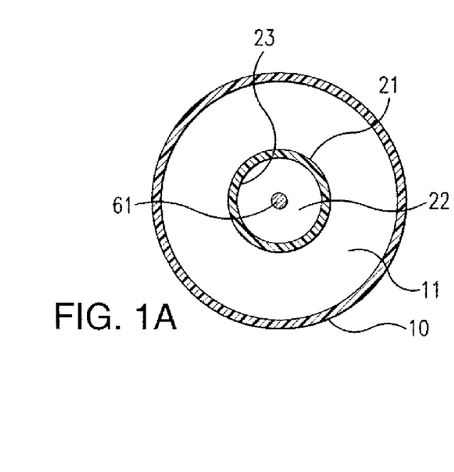
FIG. 1A is a schematic cross-sectional view of the co-axial configuration of the catheter shaft along the lines B-B of FIG. 1.

For purpose of illustration and not limitation, FIG. 1 depicts an OTW coaxial shaft configuration for a balloon catheter, wherein FIG. 1A represents a cross-section of the catheter 20 at A-A of FIG. 1. The co-axial arrangement includes an outer tubular member 10 and an inner tubular member 21 with a fluid lumen 11 defined therebetween. The inner tubular member 21 defines the guidewire lumen 22 therethrough. The guidewire lumen 22 receives a guidewire 61 therethrough. The inner tubular member 21 extends beyond the distal end of the outer tubular member 10 in this embodiment. FIG.

The inner tubular member 21 has a proximal end portion, a distal end portion, and a length. As depicted in the co-axial configuration of FIG. 1, the inner tubular member 21 is positioned within the outer tubular member 10 and is made of dimensions and material suitable for the intended use. For example, for purpose of cardiovascular indications, the outer tubular member 10 can have an outer diameter ranging between approximately 0.008 to 0.04 inches. Accordingly, the inner tubular member 21 has a diameter less than the diameter of outer tubular member 10. Other dimensions likewise are possible.

As embodied herein, the catheter 20 can further include a balloon 30. For purpose of example, and not limitation, the balloon 30 embodied herein is sealingly coupled to the outer tubular member 10 and the inner tubular member 21. The balloon 30 defines an interior volume in communication with the fluid lumen 11. The balloon 30 is depicted in an inflated condition in the drawing of FIG. 1. In another embodiment, the balloon 30 can have a drug coating on the balloon to deliver the drug to the lesion site. Additionally, or alternatively, a stent can be mounted on an exterior surface of the balloon 30. Examples of various known catheters and stents are disclosed in U.S. Pat. Nos. 5,649,977; 5,464,650; 5,591,227; 7,378,105; 7,445,792; 7,335,227, each of which is hereby incorporated by reference in its entirety. Examples of other balloon and catheter embodiments which can be employed in accordance with the disclosed subject matter include, for purpose of illustration and not limitation, U.S. Pat. Nos. 4,748,982; 5,496,346; 5,626,600; 5,300,085, 6,406, 457 and U.S. application Ser. Nos. 12/371,426; 11/539,944; 12/371,422, each of which is hereby incorporated by reference in its entirety.

Figure 1B:
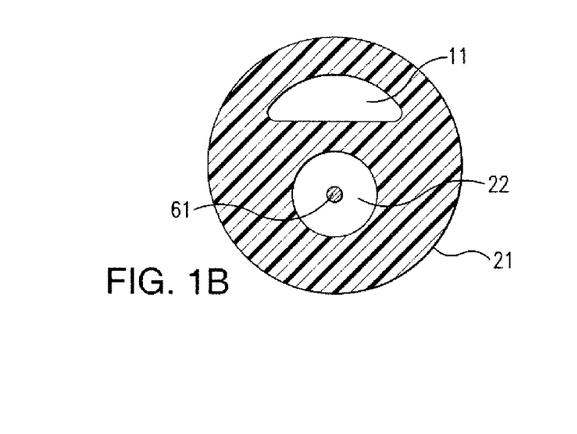
FIG. 1B is a schematic cross-sectional end view of a monolithic shaft, according to an alternative embodiment of the disclosed subject matter.

In an alternative embodiment, the shaft of the catheter 20 includes a single piece multi-lumen member. In this embodiment as schematically shown in FIG. 1B in cross-section, the shaft has multi-lumens including a fluid lumen 11 and a guidewire lumen 22 for purpose of example. Accordingly, at least the distal section of the catheter can be either a multi-lumen or a co-axial configuration, as described above. Furthermore, the disclosed subject matter is not limited to balloon catheters.

According to the embodiment of FIG. 1, the inner tubular member 21 has an interior wall surface 23 defining the guidewire lumen 22 that extends longitudinally through at least a portion of the tubular member 21. The interior wall surface 23 includes an inner stop 28, as depicted in FIG. 1. Generally, the inner stop defines a surface partially obstructing the lumen 22 of the inner tubular member 21. The inner stop 28 can define an abrupt surface, as shown, or a contoured surface, such as an angled or arcuate surface if desired. The inner stop 28 extends inwardly from the interior wall 23 of the inner tubular member at the distal end section of the catheter. In embodiments including a balloon 30, such as depicted in FIG. 1, the inner stop 28 can be positioned distal to a distal end of the balloon 30 to prevent kinking or pinching of the balloon.

Figure 3:
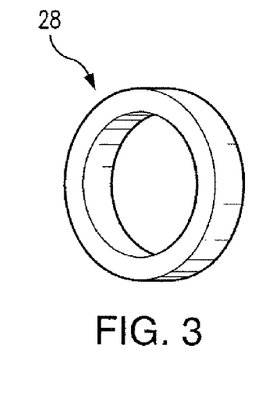
FIG. 3 is a schematic perspective view of an example of an inner stop formed with a closed ring, according to the disclosed subject matter.
Figure 4:
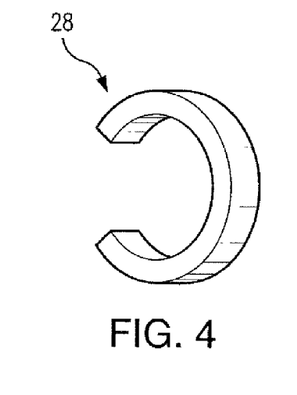
FIG. 4 is a schematic perspective view of an example of an inner stop formed with an open ring, according to the disclosed subject matter.

The inner stop can have a plurality of suitable construction and configurations. In one embodiment, the inner stop 28 comprises a ring shape. The inner stop 28 can be a closed ring member as shown in FIG. 3 or an open ring member, as depicted schematically in FIG. 4. Alternatively, the stop member can be one or more projections extending inwardly from the inner wall surface, such as radially inward directed protrusions spaced circumferentially about the inner wall surface.

The inner stop 28 can be monolithic with the inner tubular member 21 or can be one or more separate members coupled to the interior wall 23 of the tubular member. In the latter configuration, the inner stop can be coupled to the interior wall in a plurality of suitable ways. For example, but not limited to, the inner stop 28 can be swaged or embedded into the interior wall 23. In addition, the inner stop 28 can be adhered to the interior wall 23. Other known techniques, such as securing the inner stop by adhesives, thermal bonds or mechanical techniques such as, but not limited to, a press-fit, a self tapping screw mechanism, or the like can be used.

The inner stop 28 can comprise a plurality of suitable materials including, but not limited to, a rigid material, metal, metal alloy, or radiopaque material or a radiopaque loaded polymer such as disclosed in U.S. Ser. No. 11/455,382, which is incorporated herein by reference in its entirety. Additionally or alternatively, the inner stop 28 can include reinforced polymeric materials, ceramics, or substantially rigid polymeric material such as, for example, PolyEtherEtherKetone (PEEK). The inner stop can furthermore be coated with a hydrophilic coating, a hydrophobic coating, or other lubricious materials such as, for example, polytetrafluoroethylene (PTFE) or silicon.

The catheter 20 can further include one or more radiopaque markers. The location of the markers can depend on the size of the balloon. Further embodiments of catheters having marker configurations are described in U.S. Pat. No. 7,833,597; U.S. Pat. No. 7,322,959; U.S. Pat. No. 7,303,798; U.S. application Ser. No. 11/775,480; and U.S. application Ser. No. 12/945,566, the contents of which are herein incorporated by reference in their entirety.

Figure 2:
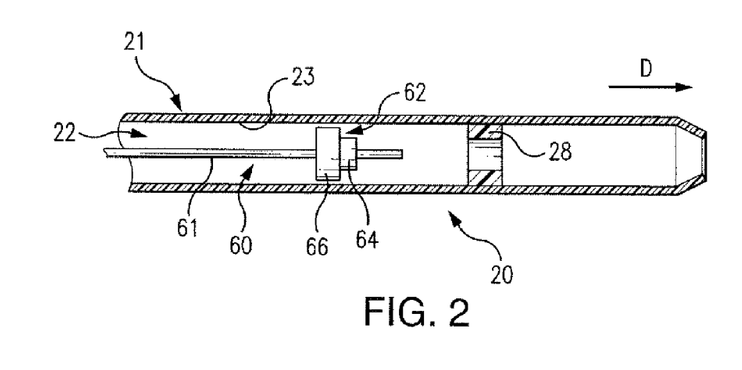
FIG. 2 is an enlarged detail of a distal end of an elongate tubular member with a pusher device inserted therein, according to the disclosed subject matter.

Further in accordance with the disclosed subject matter, a pusher device is provided for use in conjunction with the catheter having an inner stop. As embodied herein, for illustration and not limitation, FIG. 2 shows a distal end of the catheter 20 associated with the pusher device 60. The pusher device 60 is insertable into the lumen 22 of the inner tubular member 21, as depicted in FIGS. 1 and 2. In accordance with one aspect of the disclosed subject matter, the pusher device 60 can include guidewire 61 having a contact surface 62 configured to interface or abut with the inner stop 28. The contact surface 62 can be a separate member coupled to a distal end of the guidewire 61 or can be formed monolithic with the guidewire 61.

The contact surface 62 is configured to interface with the inner stop 28 of the inner tubular member 21. The contact surface 62 abuts the inner stop 28 of the inner tubular member 21 to push the catheter in a distal direction D. The contact surface 62 therefore is dimensioned to engage the proximal side of the inner stop 28. With reference to the catheter for cardiovascular indications, the guidewire 61 can have a diameter ranging between approximately 0.008 to 0.035 inches. Together, the contact surface 62 interfacing with the inner stop 28, pushes the catheter in the distal direction D.

The contact surface 62 can comprise a plurality of suitable configurations. As embodied herein, for purpose of example, FIG. 1 schematically shows the contact surface 62 as a stepped or pushpin configuration. A smaller element 64 of the configuration is dimensioned to insert through a central opening of the inner stop 28 and a larger element 66 abuts the proximal surface of the inner stop 28. Rather than a stepped configuration as depicted, the proximal side of the inner stop can be provided with a beveled or arcuate shape defining a ramp toward a central opening and the contact surface can be provided with a corresponding frustroconical or arcuate shape to mate with the proximal side of the inner stop. In this manner, a conventional guidewire can be directed toward the central opening when inserted through the inner stop.

Figure 5:
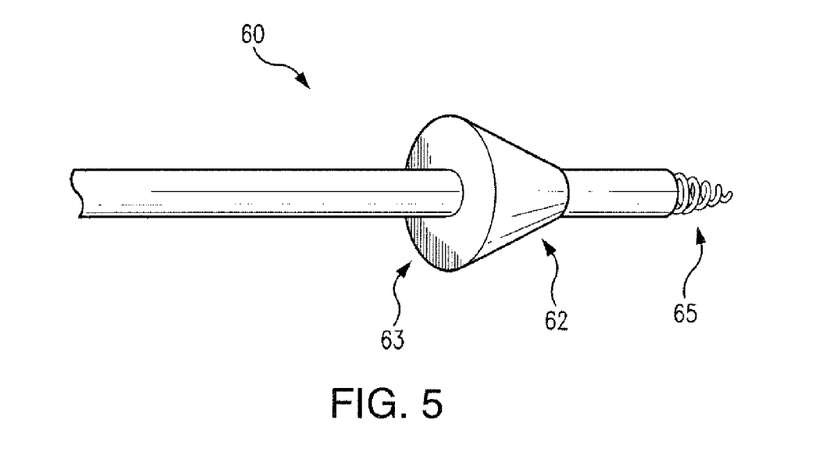
FIG. 5 is a schematic perspective of a pusher device with a flange and flexible tip, according to the disclosed subject matter.

In another embodiment as depicted in FIG. 5, the contact surface 62 is defined by a flange 63 extending outwardly from the guidewire 61. The contact surface 62 can be configured to correspond, or even mate, with the surface of the inner stop 28. In this manner, the flange 63 can have any of a plurality of suitable configurations and/or orientations including, but not limited to, a stepped configuration, a ring shape, a plurality of outwardly extending projections, or any suitable geometric shape, such as a cone or frustroconical shape as depicted in FIG. 5 for purpose of illustration and not limitation.

Figure 6:
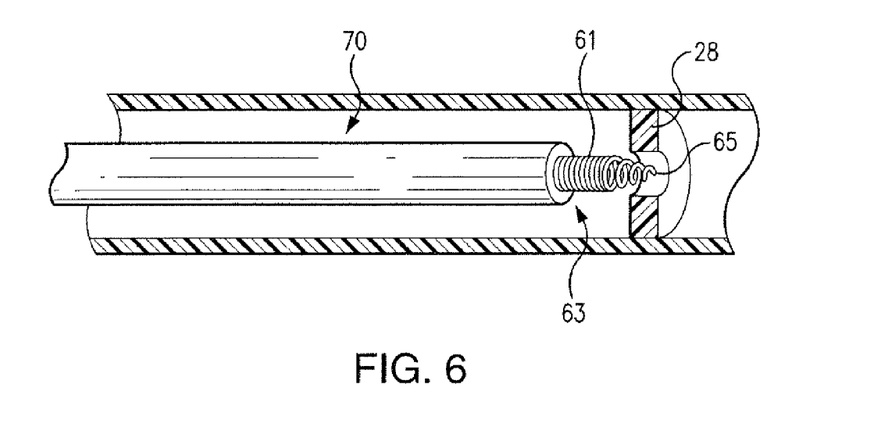
FIG. 6 is a schematic cross-sectional side view of an alternative embodiment of an inner tubular member with an alternative pusher device, according to the disclosed subject matter.

The pusher device 60 can also include a flexible tip 65. The tip 65 is located at the distal end of the pusher device 60 and distal to the contact surface 62. The flexible tip 65 can include any of a plurality of suitable configurations as known for conventional guidewires or the like including, but not limited to, a helical or spiral end as depicted in FIGS. 5 and 6 respectively. The tip 65 is insertable distally through the lumen 22 beyond the inner stop 28, and atraumatic if extending beyond the distal end of the catheter.

The tip 65 of the pusher device can be formed as a separate element coupled to the guidewire 61 or monolithic with the guidewire 61. For purposes of illustration and not limitation, in one embodiment the tip 65 has a generally cylindrical shape as depicted in FIG. 5, and in another embodiment has a distal tapered section as depicted in FIG. 6. Alternatively, the tip 65 of the pusher device can be molded from a relatively soft material, which may be softer than the tubular member 21 to reduce trauma to the vasculature of a patient. According to one embodiment, the tip can be a coiled tip. It is further contemplated that the tip 65 may be made of a material that is harder and/or has greater stiffness than the tubular member 21. The tip 65 can also include a radiopaque material Various other suitable dense materials such as, but not limited to, Platinum-Iridium, Tungsten, Tantalum, Gold, and Silver can be used for the tip to avoid flaring when the pusher device abuts the inner stopper such as when the pusher 60 is made of PEEK or the like.

In accordance with another aspect of the disclosed subject matter, the pusher member can include or be in the form of a sleeve. For purpose of illustration and not limitation, FIG. 6 depicts the disclosed subject matter in which the pusher device 60 comprises a sleeve 70 having a distal contact surface 63. The sleeve 70 comprises a length, a diameter, and a lumen extending therethrough. The sleeve of this embodiment is sized to be received over the guidewire but fit within the guidewire lumen of the inner tubular member. In this manner the guidewire 61 and sleeve 70 are insertable into the lumen 22 of the inner tubular member 21, such that the sleeve 70 engages with the inner stop 28 of the inner tubular member 21—either directly if no contact surface is provided on the guidewire or indirectly with the contact surface of the guidewire therebetween. Furthermore, the guidewire and sleeve can be configured to lock or be secured together if desired, so as to allow the two members to be inserted together simultaneously as a single pusher device. The sleeve 70 of this embodiment is configured to allow for increased pushability against the stop to urge the catheter in a distal direction yet have suitable flexibility.

The pusher device 60 and/or sleeve 70 (if provided) can be made from a variety of suitable materials including, but not limited to, metallic material such as stainless steel, such as 304V stainless steel, 316 L stainless steel, elgiloy, cobalt chromium (CoCr) alloys, or nickel-titanium alloy. Additionally or alternatively, the pusher device 60 can be made of or reinforced with a cable wire to increase flexibility. Such cable wires, as those produced by Asahi Intecc, are well known in the art and can be produced with a thin wall while exhibiting good flexibility and column strength. The pusher device 60 and/or sleeve 70 can include other suitable materials with good axial stability and good column strength. Further still, the sleeve may be constructed of multiple elements to form a longitudinal sleeve member, as discussed in greater detail below.

Additionally or alternatively, the pusher device 60 and/or sleeve 70 can comprise a suitable polymeric material of sufficient compressive strength and flexibility, such as a thin wall member made of, but not limited to, PEEK or other suitable polymeric material. Additionally, the polymeric material can be reinforced to increase column strength. Reinforcement of the pusher device 60 and/or sleeve 70 can include, but is not limited to, metallic braiding, short fiber reinforcement, long fiber reinforcement, and liquid crystal reinforcement. The polymeric pusher device 60 and/or sleeve 70 can also be stretched to achieve a high orientation.

Figure 7:
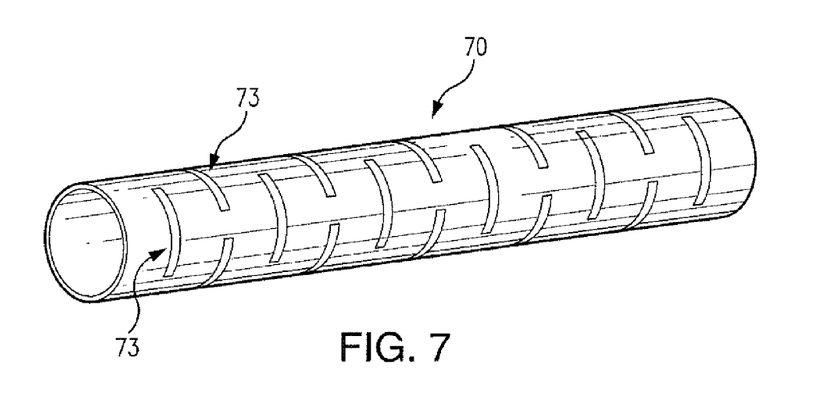
FIG. 7 is a schematic perspective view of a pusher device in the form of a sleeve, according to an alternative embodiment of the disclosed subject matter.

For increased flexibility with suitable pushability, the sleeve can be formed of a coil or the like. Alternatively, and as embodied herein, the sleeve 70 can comprise a tubular member with a plurality of slots 73 defined therein and spaced along the length of the sleeve, as depicted in FIG. 7. The size, shape, and spacing of the slots 73 can be selected to provide the desired flexural characteristics of the sleeve 70 in a predetermined manner. For example, alternating pairs of slots 73 can be disposed circumferentially with respect to each other by a predetermined angle, such as 90 degrees. Additionally or alternatively, the slots can be spaced longitudinally along the sleeve to provide constant or varied flexibility as desired.

Figure 8:
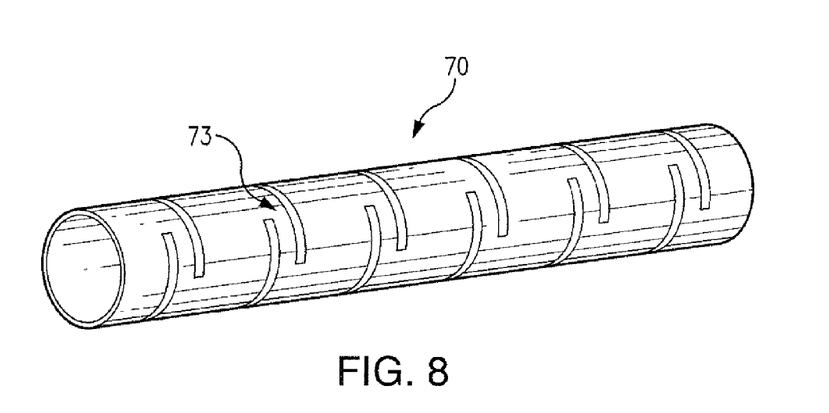
FIG. 8 is a schematic perspective view of an alternative sleeve of the disclosed subject matter.

FIGS. 7 and 8 depict examples of a sleeve with slots 73 that are offset and overlapping in different patterns. The longitudinal spacing between perforations can be varied to provide for varying rigidity or flexibility along the length of sleeve 70. Likewise, the circumferential placement of slots 73 about sleeve 70 can be varied to impart desired bending characteristics to sleeve 70. Other suitable shapes and arrangements in accordance with the invention are contemplated. Additional details regarding the use of selected slots to introduce desired flexural characteristics in a tubular member are disclosed in U.S. Publication No. 2005/0182475, the disclosure of which is incorporated by reference in its entirety.

Figure 9:
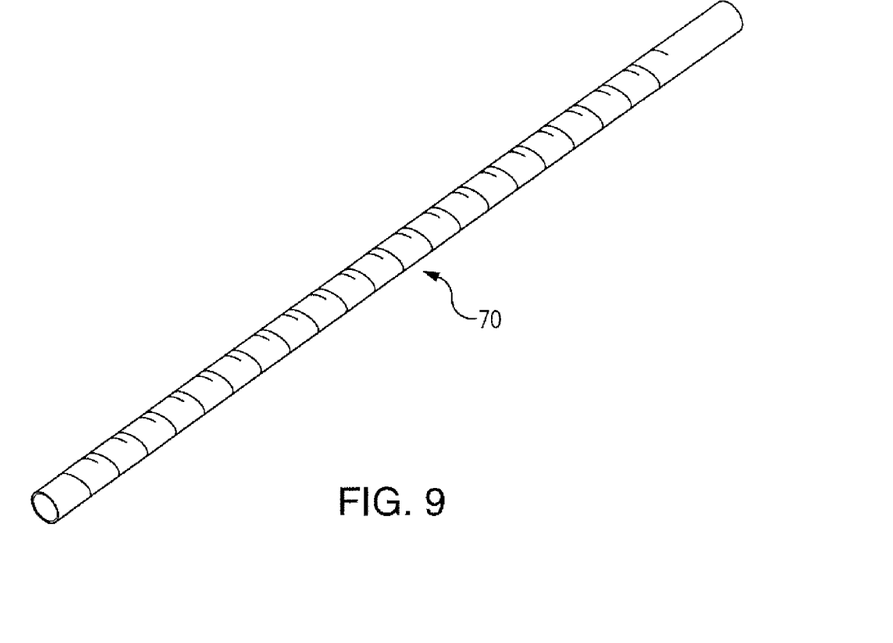
FIG. 9 is a perspective view of a pusher device in the form of a sleeve with curvilinear slots, according to an embodiment of the disclosed subject matter.
Figure 10:
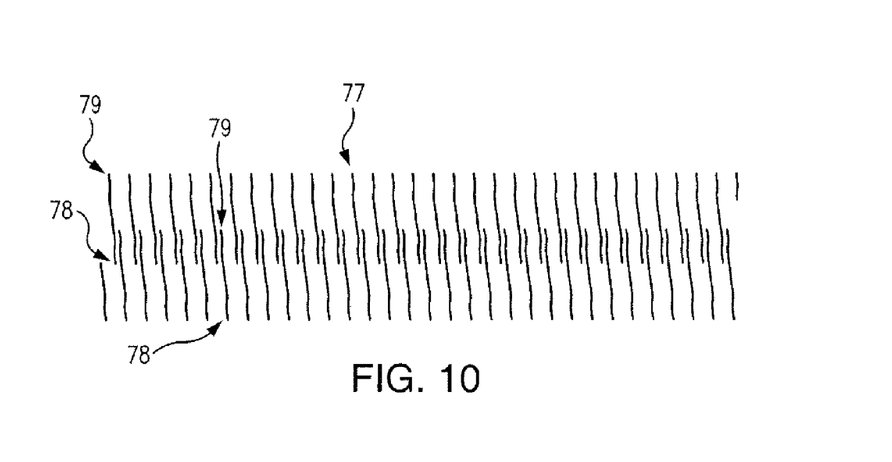
FIG. 10 is a representative embodiment of the pattern of curvilinear slots of FIG. 9, according to the disclosed subject matter.
Figure 11:
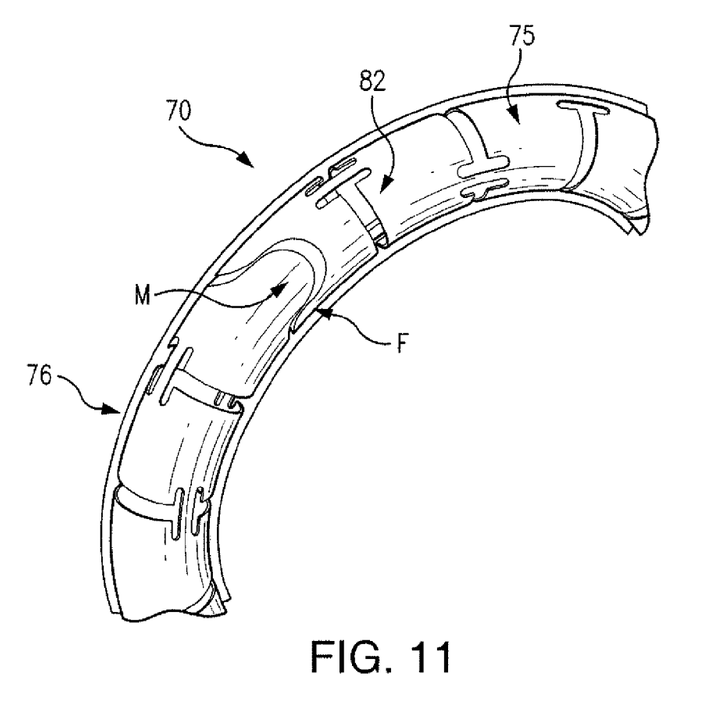
FIG. 11 is a perspective view of an alternative embodiment of the pusher device in the form of a plurality of tubular components encased in a jacket, according to an aspect of the disclosed subject matter.

The slot likewise can be provided with a variety of shapes. For example, the slots can be curvilinear slots 77 and extend around a circumference of the sleeve, as depicted in FIGS. 9 and 10. Each curvilinear slot 77 has a length, a first end 78 and a second end 79. Each respective curvilinear slot 77 is longitudinally offset from an adjacent curvilinear slot. Thus, the first end 78 of a respective slot can be disposed a circumferential location different than the first end 78 of an adjacent slot, as depicted in FIG. 10. By way of example and not of limitation, the shape of the slot 77 can also be helical, curved, or a combination of the above. Further, the slots 77 can include longitudinal components, such as an I-shape 82, as depicted in FIG. 11.

Figure 12:
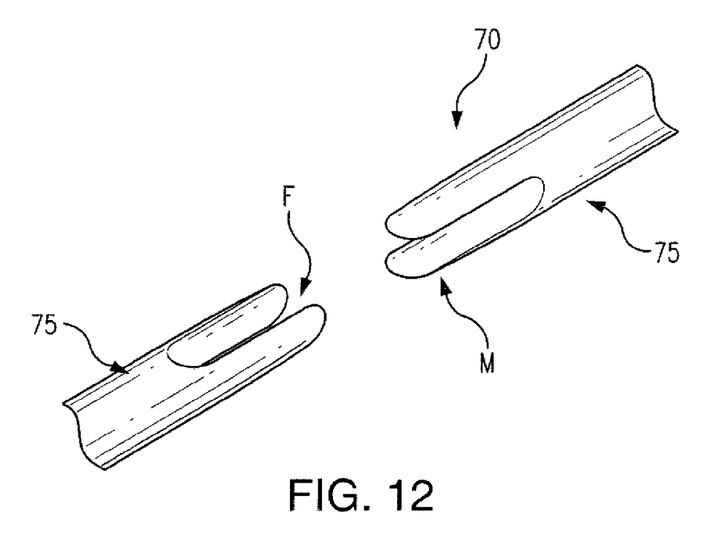
FIG. 12 is a schematic perspective view of a representative interconnection between adjacent tubular components, according to another embodiment of the disclosed subject matter.

The sleeve 70 can be a single monolithic member. Alternatively, and in accordance with another embodiment, the sleeve can comprise a plurality of tubular components 75 interconnected together. For example, a series of short length tubular components can be joined together with a thin-walled jacket or the like, such as a polymer film or membrane. Additionally, or alternatively, and as depicted in FIGS. 11 and 12, the tubular components can be provided with male and female interfaces. The male interface M of one tubular component can couple with the female interface F of an adjacent component. Hence, the adjacent tubular components provide suitable pushability, and the male and female interfaces are configured to allow for transverse movement and increased flexibility of the sleeve as a whole. Each respective tubular component 75 has a length, a diameter, and a lumen extending therethrough. Additionally, the components may be encased in a jacket 76 to form a single continuous tubular member.

The pusher device whether in the form of a guidewire or a sleeve can further comprise a radiopaque material. For example, the pusher device 60 can be made of at least in part of radiopaque material or a radiopaque coating can be applied to the pusher device 60. In one embodiment, the radiopaque material is localized at the slot surface of the pusher device. Examples of radiopaque material include, but are not limited to, platinum, tantalum, tungsten, gold, niobium, silver, or other metal material with a substantially high density barium sulfate, iodine, or a polymer filled with one of the above mentioned metals, or an alloy or combination thereof. United States Publication Number 2011/0070355 to Bavaro et al. and U.S. Pat. No. 7,303,798 to Bavaro et al., U.S. Pat. No. 7,322,959 to Warnack at al., and U.S. Pat. No. 7,833,597 to Bavaro et al. discuss further examples of radiopaque materials and the disclosures of which are herein incorporated by reference in their entirety.

The pusher device can cooperate with the catheter in a plurality of suitable manners to allow for and enable a wide variety of methods of using the medical device as disclosed. For purpose of illustration and not limitation, a few possible methods described with reference to the medical device systems embodied herein. For example, the method includes providing a catheter 20 including the elongate tubular member 21 having an inner wall surface 23 defining a lumen extending longitudinally through at least a portion of the tubular member and an inner stop 28 extending inwardly from the interior wall surface 23 of the tubular member at a distal end section of the catheter. The catheter is positioned within a body lumen and a pusher device is inserted into the lumen 22 of the elongate tubular member. The pusher device includes a contact surface 62 to abut against the inner stop of the tubular member.

In one embodiment, such as in an OTW configuration, the catheter can be inserted over a conventional guidewire previously positioned in the luminal system of a patient. Due to an occlusion or the tortuous passageway to a lesion site, the catheter can become lodged in the luminal system and be unable to move further distally. In this embodiment, the conventional guidewire can subsequently be removed while maintaining the catheter in place in the luminal system. The pusher device can be inserted into the lumen of the elongate tubular member to urge the catheter distally within the passageway of the luminal system. In this manner, the contact surface of the pusher device abuts the inner stop of the catheter to provide the necessary force to urge the catheter distally. As previously described, the contact surface can be in the form of a flange on a guidewire member and/or in the form a sleeve. The sleeve can be provided subsequent to placement of the guidewire, or can be inserted simultaneously with the guidewire as previously described above.

In an alternate embodiment, such as in an RX configuration, the conventional guidewire can remain in the luminal system of the patient. In this embodiment, a pusher device in the form of a sleeve can be inserted over the conventional guidewire through the proximal guidewire port. The sleeve can abut the inner stop 28 extending inwardly from the interior wall surface 23 of the tubular member to urge or assist in urging the catheter distally. Other suitable methods of delivering the medical device are contemplated herein.

In addition to the various embodiments depicted and claimed, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Many modifications, variations, or other equivalents to the specific embodiments described above will be apparent to those familiar with the art. It is intended that the scope of this disclosed subject matter be defined by the claims below and those modifications, variations and equivalents apparent to practitioners familiar with this art.

What is claimed is:

1. A medical device system, comprising:
    a catheter including
        an elongate tubular member having an inner wall surface defining a lumen extending longitudinally through at least a portion of the tubular member, and
        an inner stop extending inwardly from the inner wall surface of the tubular member at a distal end section of the catheter, wherein the inner stop is discontinuously spaced about the inner wall surface; and
    a pusher device independently insertable into the lumen, the pusher device having a contact surface to abut the inner stop of the tubular member.

2. The medical device system according to claim 1, wherein the catheter further includes
    an outer tubular member, wherein the elongate tubular member is disposed within the outer tubular member; and
    a balloon coupled to a distal end of at least one of the outer tubular member and the elongate tubular member.

3. The medical device system according to claim 2, wherein the inner stop is distal to a distal end of the balloon.

4. The medical device system according to claim 1, wherein the inner stop is coupled to the inner wall surface of the tubular member.

5. The medical device system according to claim 1, wherein the inner stop is made of a metal, metal alloy, or radiopaque material.

6. The medical device system according to claim 1, wherein the inner stop comprises a ring member.

7. The medical device system according to claim 1, wherein the inner stop includes a coating on an inside surface of the inner stop, the coating including one of polytetrafluoroethylene coating, hydrophilic coating, hydrophobic coating, or silicon coating.

8. The medical device system according to claim 1, wherein the inner stop defines an abrupt surface partially obstructing the lumen of the tubular member.

9. The medical device system according to claim 1, wherein the pusher device comprises a guidewire having the contact surface coupled to a distal end thereof.

10. The medical device system according to claim 9, wherein the contact surface is defined by a flange extending outwardly from the guidewire.

11. The medical device system according to claim 1, wherein the contact surface comprises a radiopaque material.

12. The medical device system according to claim 1, wherein the contact surface comprises a ring at a distal end of the pusher device.

13. The medical device system according to claim 1, wherein the pusher device comprises an elongate member with a flexible tip distal to the contact surface.

14. The medical device system according to claim 13, wherein the flexible tip is insertable distally through the lumen beyond the inner stop.

15. The medical device system according to claim 1, wherein the pusher device has an outer diameter ranging between approximately 0.008 inches and 0.035 inches.

16. The medical device system according to claim 1, wherein the elongate tubular member comprises an outer diameter ranging between approximately 0.015 to 0.04 inches.

17. The medical device system according to claim 1, wherein the pusher device comprises a sleeve defining the contact surface.

18. The medical device system according to claim 17, wherein the sleeve is insertable within the lumen of the tubular member with a guidewire extending therethrough.

19. The medical device system according to claim 17, wherein the sleeve comprises a tubular component having a length, a diameter, and a lumen extending therethrough, wherein the sleeve has a plurality of circumferentially-extending slots defined therein spaced along the length of the tubular component, wherein one or more of the plurality of slots are curvilinear and each respective curvilinear slot is circumferentially offset from an adjacent curvilinear slot.

20. The medical device system according to claim 17, wherein the sleeve comprises a tubular component having a length, a diameter, and a lumen extending therethrough, wherein the sleeve has a plurality of circumferentially-extending slots defined therein spaced along the length of the tubular component, wherein one or more of the plurality of slots are curvilinear and each respective curvilinear slot is longitudinally offset from an adjacent curvilinear slot.

21. The medical device system according to claim 17, wherein the sleeve comprises a plurality of tubular components interconnected together wherein the plurality of tubular components are encased in a jacket.

22. The medical device according to claim 1, wherein the pusher device comprises at least one of metallic material, stainless steel, 304V stainless steel, 316 L stainless steel, elgiloy, cobalt chromium (CoCr) alloys, nickel-titanium alloy, PEEK, polymeric material, reinforced polymeric material, or a cable wire.

23. The medical device according to claim 1, wherein the inner stop comprises an open ring member.

24. The medical device according to claim 1, wherein the inner stop comprises at least one projection extending inwardly from the inner wall surface.

25. The medical device according to claim 24, wherein the at least one projection includes radially inward directed protrusions spaced circumferentially about the inner wall surface.

26. The medical device according to claim 1, wherein the pusher device is movable proximally with respect to and independent of the catheter.

27. A method of delivering a medical device, comprising:
providing a catheter including an elongate tubular member having an inner wall surface defining a lumen extending longitudinally through at least a portion of the tubular member and an inner stop extending inwardly from the inner wall surface of the tubular member at a distal end section of the catheter, wherein the inner stop is discontinuously spaced about the inner wall surface;
positioning the catheter in a body lumen; and
independently inserting a pusher device into the lumen of the elongate tubular member, wherein the pusher device comprises a contact surface to abut against the inner stop of the tubular member.

28. The method of delivering a medical device according to claim 27, further comprising advancing the catheter in the distal direction by urging the pusher device distally with the contact surface abutting the inner stop distally.

29. The method of delivering a medical device according to claim 27, wherein the pusher device comprises a sleeve defining the contact surface.

30. The method of delivering a medical device according to claim 27, wherein the pusher device is a guidewire having the contact surface to interface with the inner stop of the tubular member.

31. The method of delivering a medical device according to claim 30, wherein the pusher device is a sleeve.

32. The method of delivering a medical device according to claim 27, further comprising locating a guidewire within the lumen of the tubular member, and inserting a sleeve over the guidewire to comprise the contact surface.

* * * * *